US00PP34104P2

(12) United States Plant Patent
Beekenkamp

(10) Patent No.: US PP34,104 P2
(45) Date of Patent: Apr. 5, 2022

(54) ***DAHLIA* PLANT NAMED 'BKDAMOR'**

(50) Latin Name: *Dahlia hybrida*
Varietal Denomination: BKDAMOR

(71) Applicant: BEEKENKAMP PLANTS B.V., Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/346,280

(22) Filed: Jun. 13, 2021

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — C. Anne Whealy

(57) ABSTRACT

A new and distinct cultivar of *Dahlia* plant named 'BKDAMOR', characterized by its upright to somewhat outwardly spreading and sturdy plant habit; moderately vigorous growth habit; freely branching habit; dense and bushy growth habit; dark green-colored leaves; freely flowering habit; decorative type inflorescences with orange-colored ray florets; and good garden performance.

2 Drawing Sheets

Figure 1:
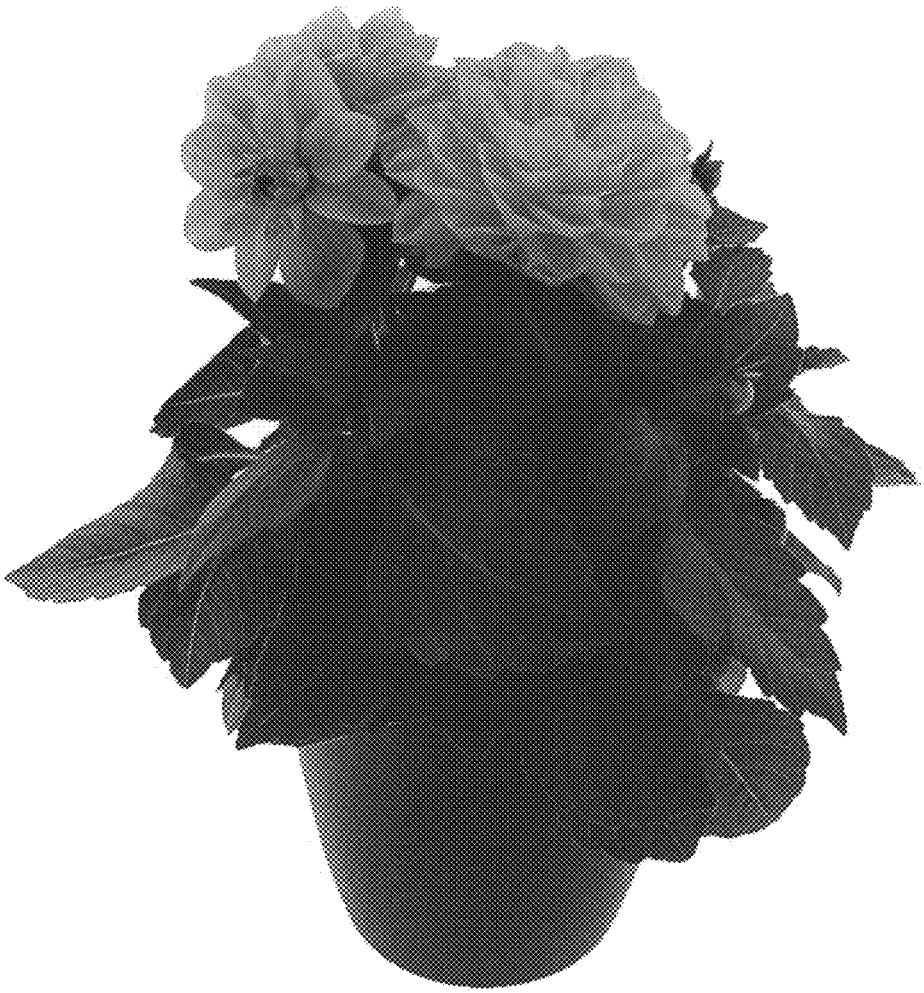

Botanical designation: *Dahlia hybrida.*
Cultivar denomination: 'BKDAMOR'.

STATEMENT REGARDING PRIOR DISCLOSURES BY INVENTOR/APPLICANT and ASSIGNEE

An European Community Plant Breeder's Rights application for the instant plant was filed by the Applicant/Assignee of the instant application, Beekenkamp Plants B.V. of Maasdijk, The Netherlands on Oct. 1, 2020, application number 2020/2421. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Dahlia* plant, botanically known as *Dahlia hybrida* and hereinafter referred to by the name 'BKDAMOR'.

The new *Dahlia* plant is a product of a planned breeding program conducted by the Inventor in Maasdijk, The Netherlands. The objective of the breeding program is to create new freely branching container *Dahlia* plants with large inflorescences and attractive ray floret coloration.

The new *Dahlia* plant originated from an open-pollination in September, 2014 in Maasdijk, The Netherlands of a proprietary selection of *Dahlia hybrida* identified as code number 12-0032-06, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Maasdijk, The Netherlands in December, 2014.

Asexual reproduction of the new *Dahlia* plant by terminal cuttings in a controlled greenhouse environment in Maasdijk, The Netherlands since March, 2016 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMOR'. These characteristics in combination distinguish 'BKDAMOR' as a new and distinct *Dahlia* plant:

1. Upright to somewhat outwardly spreading and sturdy plant habit.
2. Moderately vigorous growth habit.
3. Freely branching habit; dense and bushy growth habit.
4. Dark green-colored leaves.
5. Freely flowering habit.
6. Decorative type inflorescences with orange-colored ray florets.
7. Good garden performance.

Plants of the new *Dahlia* differ primarily from plants of the female parent selection in inflorescence size as plants of the new *Dahlia* have slightly larger inflorescences than plants of the female parent selection. In addition, ray florets of plants of the new *Dahlia* are darker orange in color than ray florets of plants of the female parent selection.

Plants of the new *Dahlia* can be compared to plants of *Dahlia hybrida* 'Baldahanni', not patented. In side-by-side comparisons, plants of the new *Dahlia* differ primarily from plants of 'Baldahanni' in inflorescence size as plants of the new *Dahlia* have larger inflorescences than plants of 'Baldahanni'. In addition, ray florets of plants of the new *Dahlia* are not as bright orange in color as ray florets of plants of 'Baldahanni'.

Plants of the new *Dahlia* can also be compared to plants of *Dahlia hybrida* 'Dahlietta Linda', not patented. In side-by-side comparisons, plants of the new *Dahlia* differ primarily from plants of 'Dahlietta Linda' in inflorescence size as plants of the new *Dahlia* have larger inflorescences than plants of 'Dahlietta Linda'. In addition, ray florets of plants of the new *Dahlia* are more orange than and not as yellow as ray florets of plants of 'Dahlietta Linda'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet (FIG. 1) is a side perspective view of a typical flowering plant of 'BKDAMOR' grown in a container.

Figure 2:
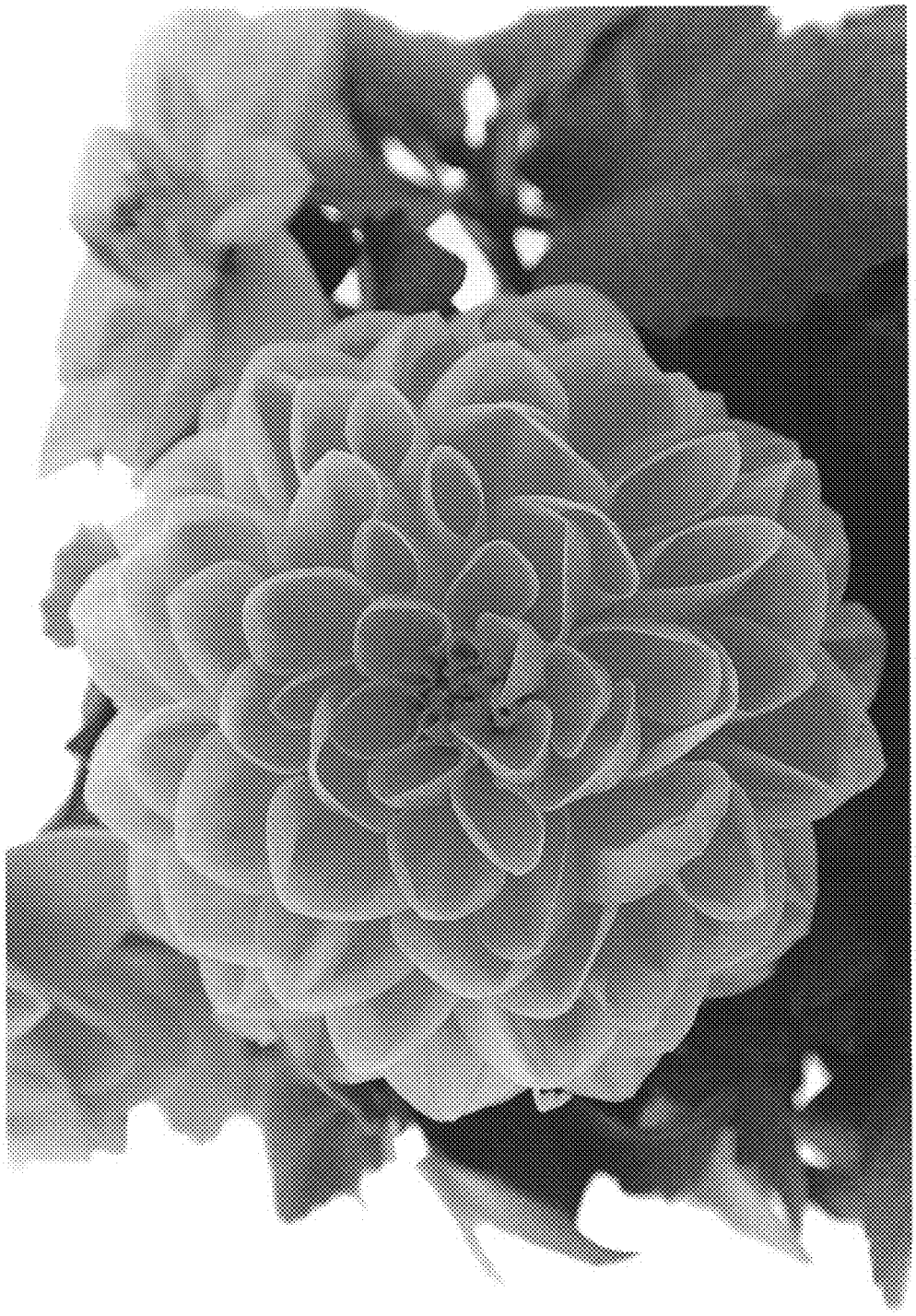

The photograph on the second sheet (FIG. 2) is a close-up view of a typical inflorescence of 'BKDAMOR'.

DETAILED BOTANICAL DESCRIPTION

The aforementioned photographs and the following observations and measurements describe plants grown during the autumn and winter in 11-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were nine weeks from planting rooted cuttings when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDAMOR'.

Parentage:

- *Female, or seed, parent*.—Proprietary selection of *Dahlia hybrida* identified as code number 12-0032-06, not patented.
- *Male, or pollen, parent*.—Unknown selection of *Dahlia hybrida*, not patented.

Propagation:

- *Type*.—By terminal cuttings.
- *Time to initiate roots, summer*.—About 16 days at temperatures ranging from 18° C. to 21° C.
- *Time to initiate roots, winter*.—About 19 days at temperatures about 21° C.
- *Time to produce a rooted young plant, summer*.—About 21 days at temperatures ranging from 18° C. to 21° C.
- *Time to produce a rooted young plant, winter*.—About 23 days at temperatures ranging from 19° C. to 21° C.
- *Root description*.—Medium in thickness, fibrous; typically creamy white to light brown in color, actual color of the roots is dependent on substrate composition, water quality, fertilizers, substrate temperature and physiological age of roots; tuber development has not been observed on plants of the new *Dahlia*.
- *Rooting habit*.—Moderately freely branching; medium density.

Plant description:

- *Plant and growth habit*.—Upright to somewhat outwardly spreading plant habit; overall plant shape, roughly flattened globular with inflorescences held above the foliar plane on strong peduncles; freely basal branching habit with about four primary branches each with about three secondary branches developing per plant; bushy and dense growth habit; pinching is not required but will improve branching habit; moderately vigorous growth habit and moderate growth rate.
- *Plant height, soil level to top of foliar plane*.—About 16 cm.
- *Plant height, soil level to top of floral plane*.—About 19.6 cm.
- *Plant diameter or spread*.—About 23.8 cm.
- *Lateral branches*.—Length: About 8.2 cm. Diameter: About 5 mm. Internode length: About 2 cm. Aspect: Primary branches are about 20° from vertical; secondary branches are about 35° from primary branch axis. Strength: Moderately strong to strong. Texture and luster: Smooth, glabrous; moderately glossy. Color, developing: Close to between 144A and 146A. Color, developed: Close to 146A.

Leaf & leaflet description:

- *Arrangement*.—Leaves opposite; simple and compound with typically three leaflets.
- *Length, simple leaves*.—About 8.2 cm.
- *Width, simple leaves*.—About 5.6 cm.
- *Length, compound leaves*.—About 7.6 cm.
- *Width, compound leaves*.—About 8.3 cm.
- *Length, terminal leaflets*.—About 7.6 cm.
- *Width, terminal leaflets*.—About 4.1 cm.
- *Length, lateral leaflets*.—About 4.6 cm.
- *Width, lateral leaflets*.—About 2.8 cm.
- *Shape, simple leaves*.—Broadly ovate.
- *Shape, compound leaves*.—Broadly deltoid in outline.
- *Shape, leaflets*.—Ovate to elliptic.
- *Apex, simple leaves and leaflets*.—Apiculate.
- *Base, simple leaves and leaflets*.—Attenuate.
- *Margin, simple leaves and leaflets*.—Coarsely crenate to bluntly senate.
- *Venation pattern, simple leaves and leaflets*.—Pinnate.
- *Texture and luster, upper surface, simple leaves and leaflets*.—Mostly smooth, glabrous with main vein, sparsely pubescent; not rugose; moderately glossy.
- *Texture and luster, lower surface, simple leaves and leaflets*.—Mostly smooth, glabrous with venation, sparsely pubescent; slightly rugose; slightly glossy.
- *Color*.—Developing simple leaves and leaflets, upper surface: Close to 137B. Developing simple leaves and leaflets, lower surface: Close to 146B. Fully expanded simple leaves and leaflets, upper surface:

Close to NN137A; venation, close to 146A and 183A. Fully expanded simple leaves and leaflets, lower surface: Close to 191A; venation, close to 146A to 146B.

*Petioles*.—Length, simple leaves: About 3.5 cm. Diameter, simple leaves: About 3 mm. Length, compound leaves: About 3.4 cm. Diameter, compound leaves: About 3 mm. Strength, simple and compound leaves: Moderately strong. Texture and luster, simple and compound leaves, upper surface: Smooth and glabrous; moderately glossy. Texture and luster, simple and compound leaves, lower surface: Smooth and glabrous; glossy. Color, simple and compound leaves, upper surface: Close to 177A; towards the margins, close to 146B. Color, simple and compound leaves, lower surface: Close to 146A.

Inflorescence description:

*Appearance and arrangement*.—Decorative type inflorescences with ray and disc florets forming acropetally on a receptacle; inflorescences positioned above and beyond the foliar plane on strong peduncles; inflorescences face mostly upright to slightly outwardly; freely flowering habit with about 30 developing and fully developed inflorescences per plant at one time.

*Fragrance*.—None detected.

*Flowering response and flowering period*.—Early flowering habit, plants begin flowering about 51 days after planting; plants flower continuously during the autumn into the winter in The Netherlands.

*Post-production longevity*.—Inflorescences maintain good substance for about ten days on the plant; inflorescences persistent.

*Inflorescence buds*.—Height: About 1.2 cm. Diameter: About 2.7 cm. Shape: Flattened globular; involucral bracts horizontal. Texture and luster: Smooth, glabrous; glossy. Color: Close to 144B; towards the base, close to 143A; towards the apex, close to 31A; involucral bracts, close to 147B.

*Inflorescence size*.—Diameter: About 8.4 cm. Depth (height): About 5 cm. Disc diameter: About 7 mm; typically inconspicuous.

*Receptacles*.—Height: About 5 mm. Diameter: About 4 mm. Shape: Ovate. Color: Close to 145C.

*Ray florets*.—Quantity per inflorescence and arrangement: About 100 arranged in about five whorls. Length: About 3.8 cm. Width: About 2.1 cm. Shape: Obovate; concave. Apex: Obtuse. Base: Attenuate. Margin: Entire. Aspect: Slightly upright to horizontal. Texture and luster, upper surface: Smooth, glabrous; velvety; matte. Texture and luster, lower surface: Smooth, glabrous; moderately velvety; matte. Color: When opening, upper surface: Close to 1A; distally, close to 21B. When opening, lower surface: Close to 1A; distally, close to 22A. Fully opened, upper surface: Close to between 13B and 14C; distally, close to 22A; venation, similar to lamina color; with subsequent development, color becoming closer to 12B and distally, close to 32A. Fully opened, lower surface: Close to 14C; distally, close to 22A to 22B; venation, close to 24A; with subsequent development, color becoming closer to 12B and distally, close to 32B.

*Disc florets*.—Quantity per inflorescence and arrangement: About ten massed at the center of the inflorescence in one or two spiral whorls; typically inconspicuous. Length: About 1.1 cm. Diameter: About 4 mm. Shape: Tubular, elongated; lower 90% fused and upper 10% free; apices, acute and reflexed. Texture and luster, inner and outer surfaces: Smooth, glabrous; glossy. Color, when opening, inner and outer surfaces: Apex and mid-section: Close to 12A. Base: Close to 154C. Color, fully opened, inner and outer surfaces: Apex: Close to 12A. Mid-section: Close to 154C. Base: Close to 145D.

*Phyllaries*.—Quantity per inflorescence and arrangement: About six in a single whorl. Length: About 1 cm. Width: About 7 mm. Shape: Oblanceolate. Apex: Broadly acute. Base: Cuneate. Margin: Entire. Texture and luster, upper and lower surfaces: Smooth, glabrous; moderately glossy. Color, upper surface: Close to 137A; towards the base, close to 146A to 146B. Color, lower surface: Close to 147B; venation, close to NN137B.

*Peduncles*.—Length, terminal peduncle: About 6.6 cm. Diameter, terminal peduncle: About 3.5 mm. Strength: Strong. Aspect: Mostly upright. Texture and luster: Smooth, glabrous; glossy. Color: Close to N199A; distally, close to 152A and proximally, close to 200B.

*Reproductive organs*.—Androecium, present on disc florets only: Quantity per floret: About five. Filament length: About 3 mm. Filament color: Close to 157D. Anther size: About 3 mm by 0.5 mm. Anther shape: Narrowly oblong. Anther color: Close to 12A. Pollen amount: Moderate. Pollen color: Close to 23A. Gynoecium, present on disc florets only: Quantity per floret: One. Pistil length: About 9 mm. Style length: About 7 mm. Style color: Close to 154D. Stigma diameter: About 3 mm. Stigma shape: Cleft to three-parted. Stigma color: Close to 13A. Ovary color: Close to 145C. Seeds and fruits: To date, seed and fruit development have not been observed on plants of the new *Dahlia*.

Pathogen & pest resistance: To date, plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAMOR' as illustrated and described.

* * * * *